United States Patent

Thompson et al.

[11] Patent Number: 5,286,251
[45] Date of Patent: Feb. 15, 1994

[54] HIP HARNESS

[76] Inventors: John K. Thompson, 2524 Old Oak Cir., Birmingham, Ala. 35243; Randall B. Keith, 4324 Willow Bend Dr., Gardendale, Ala. 35071

[21] Appl. No.: 866,414

[22] Filed: Apr. 10, 1992

[51] Int. Cl.⁵ .................................................. A61F 5/00
[52] U.S. Cl. ....................................... 602/23; 602/19; 128/100.1; 128/99.1
[58] Field of Search .................. 602/19, 23–25, 602/32, 36; 128/95.1, 96.1, 99.1, 100.1, 107.1, 112.1, 115.1, 869, 870, 876, DIG. 15; 482/92; 2/2, 22, 44, 311, 312

[56] References Cited

U.S. PATENT DOCUMENTS

| 507,172 | 10/1893 | Shelden | 602/19 |
|---|---|---|---|
| 815,747 | 3/1906 | Schmitt | 128/96.1 X |
| 894,095 | 7/1908 | Anderson | 128/112.1 X |
| 933,101 | 9/1909 | Nickum | 128/96.1 X |
| 1,008,500 | 11/1911 | Thornton | 602/19 |
| 1,548,711 | 8/1925 | Cooper | 602/25 |
| 1,812,529 | 6/1931 | Haulbrook et al. | 602/19 X |
| 2,332,119 | 10/1943 | Springer | 602/19 |
| 2,778,358 | 1/1957 | Keles | 602/19 X |
| 2,828,737 | 4/1958 | Hale | 602/19 |
| 3,295,517 | 1/1967 | Stevens | 602/19 |
| 3,872,860 | 3/1975 | Noblitt | 602/36 |
| 4,252,112 | 2/1981 | Joyce | 602/26 |
| 4,905,678 | 3/1990 | Cumins et al. | 602/19 X |
| 4,926,845 | 5/1990 | Harris | 602/19 |

Primary Examiner—Richard J. Apley
Assistant Examiner—Linda C. M. Dvorak
Attorney, Agent, or Firm—Veal & Associates

[57] ABSTRACT

A flexible hip restraint for patient's recovering from hip surgery having a waist belt, a thigh belt and a plurality of substantially inelastic flexible and adjustable straps connected to the thigh and waist belts for limiting the movement of a patient's thigh to prevent inadvertent dislocation of the femur from the pelvic socket. The straps include a posterior strap extending over the gluteus maximus, a medial strap extending over the greater trochanter and an anterior strap extending along the anterior superior iliac spine of the pelvis.

10 Claims, 3 Drawing Sheets

HIP HARNESS

FIELD OF THE INVENTION

The present invention relates to apparatus for restraining a human appendage to prevent inadvertent injury thereto. In greater particularity, the present invention relates to apparatus for restraining a patient's thigh after hip surgery to prevent inadvertent dislocation of the patient's femur from the pelvic socket.

BACKGROUND OF THE INVENTION

Various hip surgery techniques are used for repairing or replacing various bone structure in the pelvic and upper thigh regions of the human anatomy. Such surgery normally requires some incision of the muscle and tendon tissue adjacent to the pelvis such that the bone structure surrounded by such tissue may be accessed for replacement and/or repair. The muscle and tendon tissue not only facilitates movement of the skeletal hip structure but also assist in holding the femur or thigh bone within the pelvic socket.

During recovery, the muscle and tendon tissue will be substantially weakened and not completely effective in retaining the femur within the pelvic socket. Accordingly, it is common for patient's recovering from hip surgery to inadvertently move the thigh and dislocate the femur from the pelvic socket. Certain movements of the thigh will not cause dislocation and thus the patient should not be completely immobilized in most circumstances to allow some exercise of the healing muscles and tendons and to accommodate some mobility by the patient. Thigh movements commonly known to cause dislocation of the femur are the exaggerated flexion of the hip (i.e. pivoting the thigh forwardly toward the chest), adduction of the thigh toward the other leg and a combination of flexion and adduction such as crossing one leg over the other.

Several apparatus are available that prevent the movement of the thigh to such potentially damaging positions. Examples of such apparatus are shown in U.S. Pat. No. 4,481,941 issued to Rolfes; U.S. Pat. No. 4,901,710 issued to Meyer and U.S. Pat. No. 4,905,678 issued to Cumins et al. Rolfes and Cumins et al disclose a waist engaging member and a thigh engaging member having a rigid bar connected intermediate thereto that secures the thigh relative to the hip. The rigid bar has an adjustable pivotal member connected thereto to permit limited flexion of the hip. The rigid bar in Cumins et al is further designed to bias the thigh laterally and thus restrict adduction thereof. Meyer discloses a waist engaging member and thigh engaging members having a rigid frame fixably connected to the thigh engaging member and pivotally connected to the waist engaging member. The rigid frame is bent such that flexion of the hip will urge the thigh laterally.

Though Rolfes, Meyer and Cumins et al may allegedly limit the motion of the patient's thigh, a patient using the aforestated devices may be unnecessarily restrained by the overly rigid construction of such devices if the patient's hip surgery was minor or the patient is in a late stage of recovery. Even in the early stages of recovery, lighter, less bulky restraints for limiting hip motion would be advantageous to a recovering patient by limiting the weight the patient must carry. More importantly, some of these rigid devices actually promote injury to the patient while the leg is being manipulated to attach or remove the device. Further, the bulky apparatus disclosed in Rolfes, Meyer and Cumins et al would most likely have to be worn over a patient's clothes whereas a lightweight restraint designed to fit close to the patient's body would fit beneath a patient's clothes and thus facilitate a more secure grip of the patient's thigh and waist.

SUMMARY OF THE INVENTION

It is the principal object of the present invention to provide a hip restraint that will limit the movement of a patient's thigh to prevent inadvertent dislocation of the patient's femur from the pelvic socket.

Another object of the present invention is to minimize the bulk and weight of the hip restraint to maximize the patient's comfort and to allow the patient to wear the restraint under his or her clothes.

In support of the previous objects, another object of the present invention is to provide a flexible hip restraint that restrains movement of the thigh that would normally result in dislocation of the hip without restraining other thigh and hip movement that would not result in dislocation.

These and other objects and advantages of our invention are accomplished through the use of a flexible waist belt wrapped about the patient's waist, a flexible primary thigh belt wrapped about the patient's hamstrings subjacent the muscle bulk of the thigh and a plurality flexible substantially inelastic straps fixably connected to the primary thigh belt, rearwardly and laterally of the thigh. Each flexible substantially inelastic strap extends upwardly along the patient's hip and through a ring or loop connected to the waist belt. A free end of each strap has a hooked portion of hook and loop connector connected thereto that may be detachably connected to a looped portion of hook and loop connector attached to and coextending the strap such that the strap is connected to the waist belt and easily adjustable to accommodate differing dimensions in the anatomy of a variety of patients. The flexible substantially inelastic straps include a posterior strap extending over the gluteus maximum, a medial strap extending along the tensor fascia latae and across the greater trochanter and an anterior strap extending along the anterior superior iliac spine of the pelvis and forwardly of the ilium. A secondary thigh strap may be fixably connected to the flexible substantially inelastic straps above the primary thigh strap and wrapped about a mid-portion of the thigh to further restrict the movement of the patient's hip.

BRIEF DESCRIPTION OF THE DRAWINGS

Apparatus embodying features of our invention are depicted in the accompanying drawings which form a portion of this disclosure and wherein.

DESCRIPTION OF A PREFERRED EMBODIMENT

Figure 1:
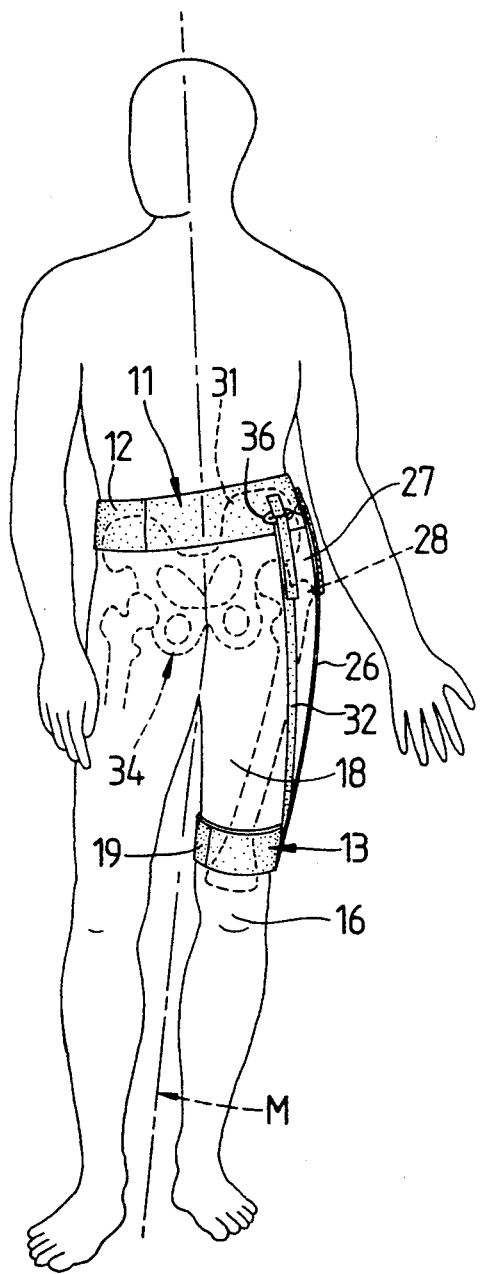
FIG. 1 is an anterior view of a human wearing a first embodiment of the present invention.
Figure 2:
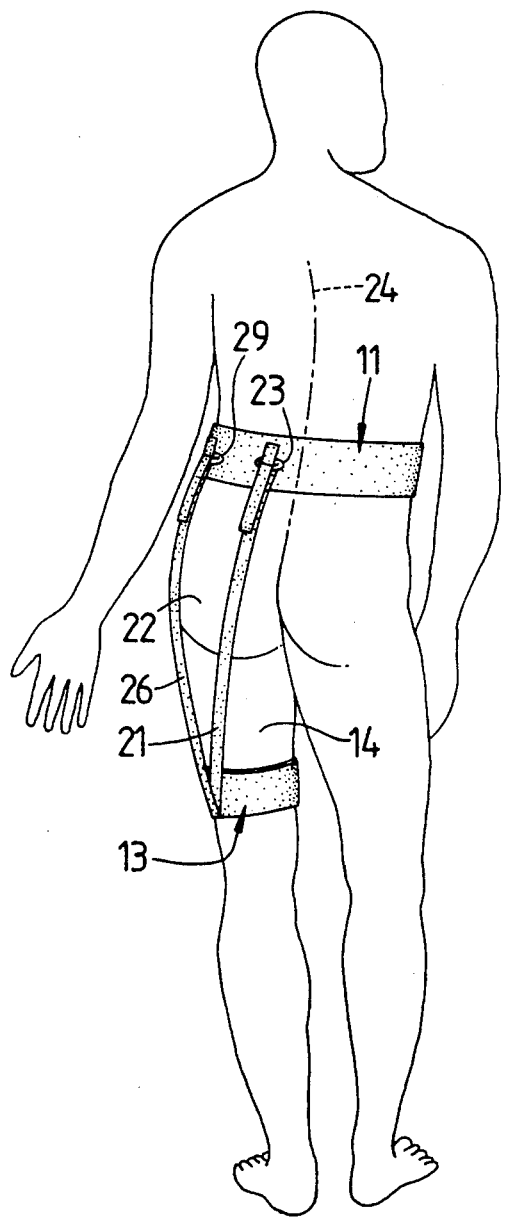
FIG. 2 is a posterior view of a human wearing the first embodiment of the present invention.
Figure 3:
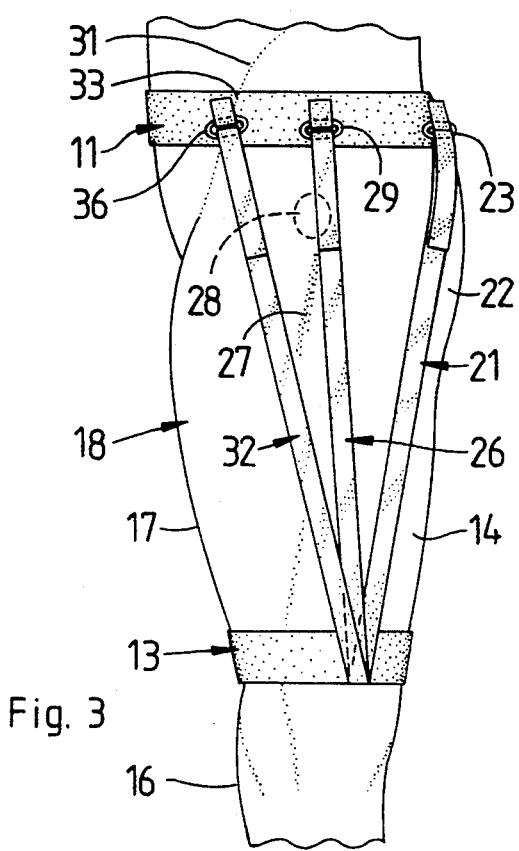
FIG. 3 is a left side view of the lower abdomen and thigh regions of a human wearing the first embodiment of the present invention.
Figure 4:
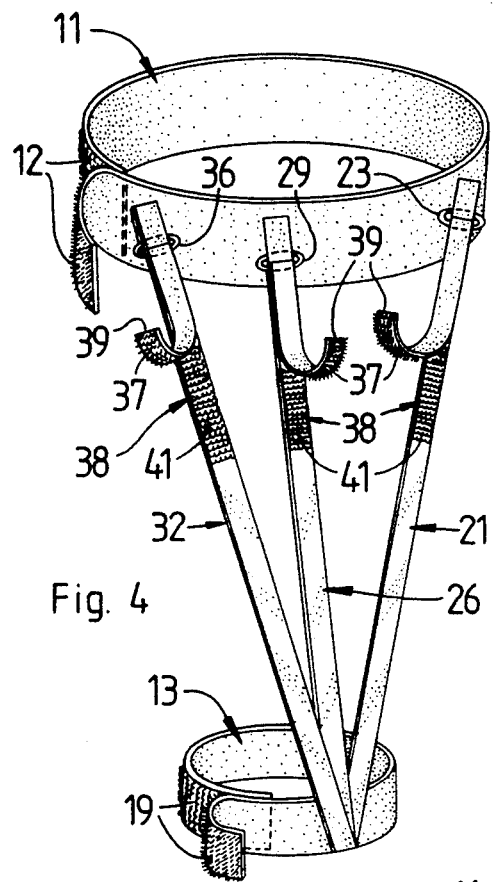
FIG. 4 is a left side view of the first embodiment of the present invention.
Figure 6:
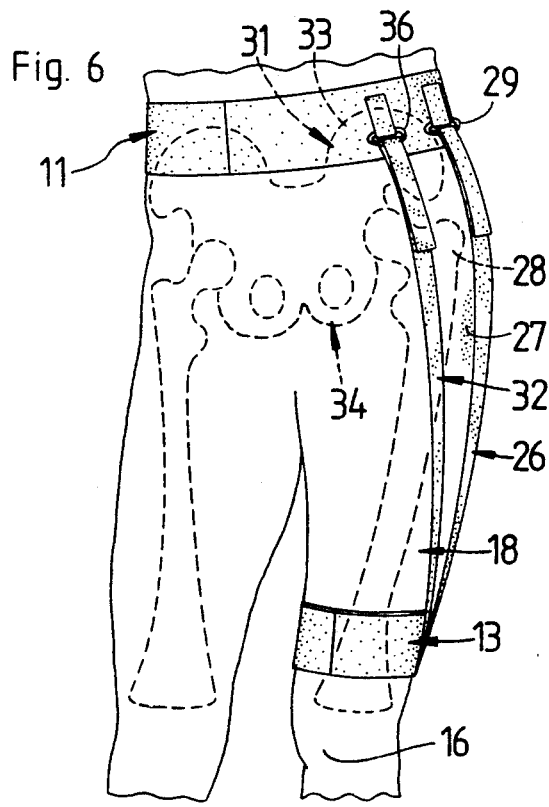
FIG. 6 is a detailed view of FIG. 1 with selected skeletal and muscular components of the human anatomy shown in phantom lines.
Figure 5:
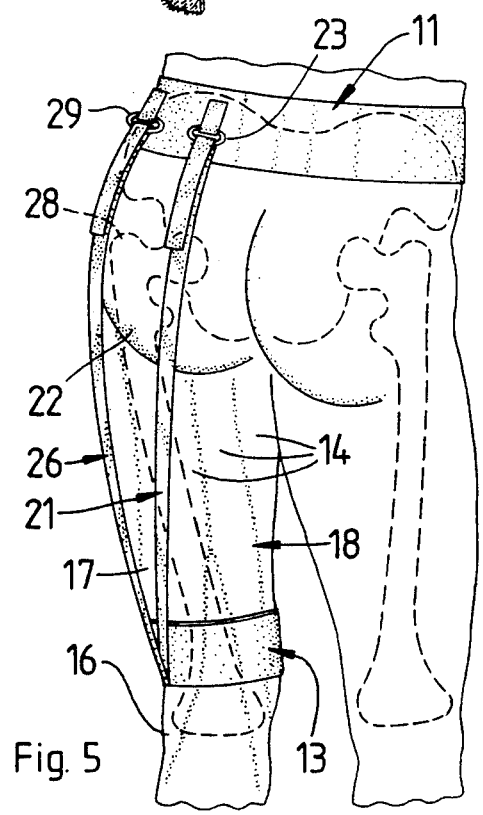
FIG. 5 is a detailed view of FIG. 2 with selected skeletal and muscular components of the human anatomy shown in phantom lines.

Referring to the drawings for a clearer understanding of the invention, it should be noted in FIGS. 1 and 2 that a first embodiment of the present invention contemplates the use of a flexible waist belt 11 encircling a patient's waist and secured thereabout by hook and loop connector 12 connected to the waist belt 11. A flexible primary thigh belt 13 is wrapped around the patient's leg 14 intermediate the knee 16 and the muscle bulk 17 of a patient's thigh 18. The primary thigh belt 13 is secured by hook and loop connector 19. As shown in FIGS. 2-5, a flexible substantially inelastic posterior strap 21 is fixably connected to the primary thigh belt 13, rearwardly and laterally of the thigh 18, and extends upwardly therefrom, over the patient's gluteus maximus 22 and through a posterior ring 23 connected to the waist belt 11 proximal to the patient's spinal column 24. As shown in FIGS. 1-6, a flexible substantially inelastic medial strap 26 is fixably connected to the primary thigh belt 13 adjacent to the posterior strap 21 and extends upwardly along the patient's tensor fascia latae 27 and across the patient's greater trochanter 28. The strap 26 extends through a medial ring 29 connected to the waist belt 11 in laterally spaced relation to the posterior ring 23 and superjacent the patient's ilium 31. A flexible substantially inelastic anterior strap 32, shown in FIGS. 1, 3, 4 and 6 is fixably connected to the primary thigh belt 13 anteriorly of thigh 18 and adjacent to the posterior and medial straps 21 and 26 and extends upwardly along the anterior superior iliac spine 33 of the patient's pelvis 34 and through an anterior ring 36 connected to the waist belt 11 in laterally spaced relation to the medial ring 29 and forwardly of the patient's ilium 31. A hooked portion 37 of hook and loop connector 38 is connected to a free end 39 of each flexible strap 21, 26 and 32. The hooked portion 37 is detachably connected to a looped portion 41 of hook and loop connector 38 that is connected to the flexible straps 21, 26 and 32 distal the free ends 39 thereof. The straps 21, 26 and 31 are thus adjustable to accommodate differences in the anatomical dimensions of various patients. The straps 21, 26 and 32 are also adjustable to vary the patient's range of hip movement. It should be noted that the ring 23, 29 and 36 may be replaced by reinforced fabric loops or other suitable means for releasably attaching straps 21, 26, and 29.

The posterior strap 21 limits flexion of the patient's hip by limiting the forward pivotal movement of the thigh 18. When the thigh 18 is pivoted forward, the posterior strap 21 is tightened against the gluteus maximus thus restraining the forward pivotal movement of the thigh 18. The range of forward thigh movement is limited by the initial tension on the posterior strap 21.

The anterior strap 32 limits the adduction of the patient's thigh 18 past the midline (indicated as M in FIG. 1) of the patient's body. By tensioning the anterior strap 32, adduction of the thigh 18 is limited at an increasingly larger angular distance laterally of the midline M.

The medial strap 26 limits both flexion and adduction and is thus supportive of the functions performed by the posterior and anterior straps. Particularly, the medial strap 26 limits the combination of flexion and adduction utilized when a patient crosses one leg over another. This common and habitual motion would present a high risk of dislocation and; thus, the medial strap is especially helpful in protecting the patient's recovering hip from inadvertent self-inflicted injury.

Figure 7:
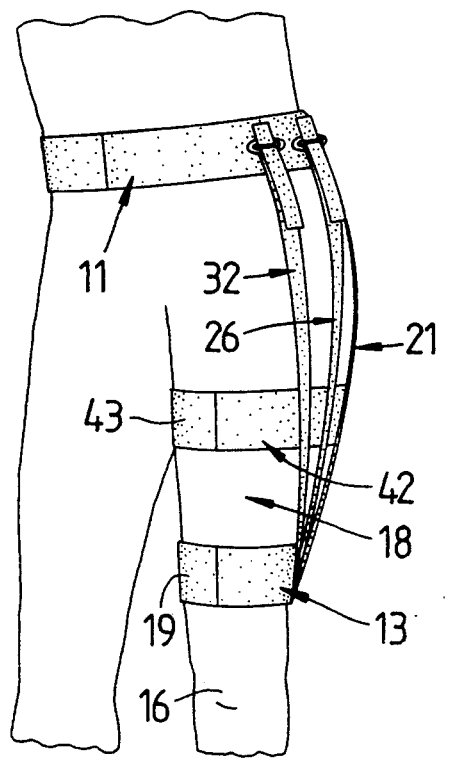
FIG. 7 is a perspective view of the lower abdomen and thigh regions of a human wearing a second embodiment of the present invention.
Figure 8:
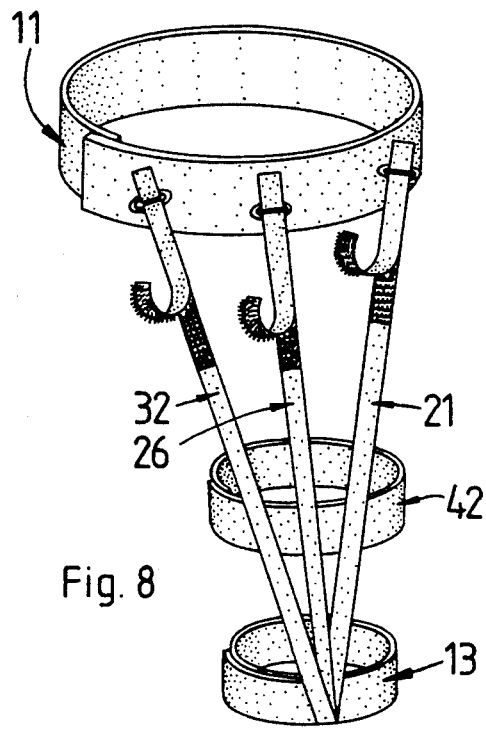
FIG. 8 is a left side view of the second embodiment of the present invention.

A second embodiment of the present invention is shown in FIGS. 7 and 8, and includes a secondary thigh belt 42 fixably connected to the flexible straps 21, 26 and 32 above the primary thigh belt 13. The secondary thigh belt is wrapped around the mid-thigh and secured thereabout by hook and loop connector 43 to stabilize the straps 21, 26 and 32 and further restrain the movement of the patient's thigh 18. Alternatively this belt may merely provide connection between the straps 21, 26 and 32.

Figure 9:
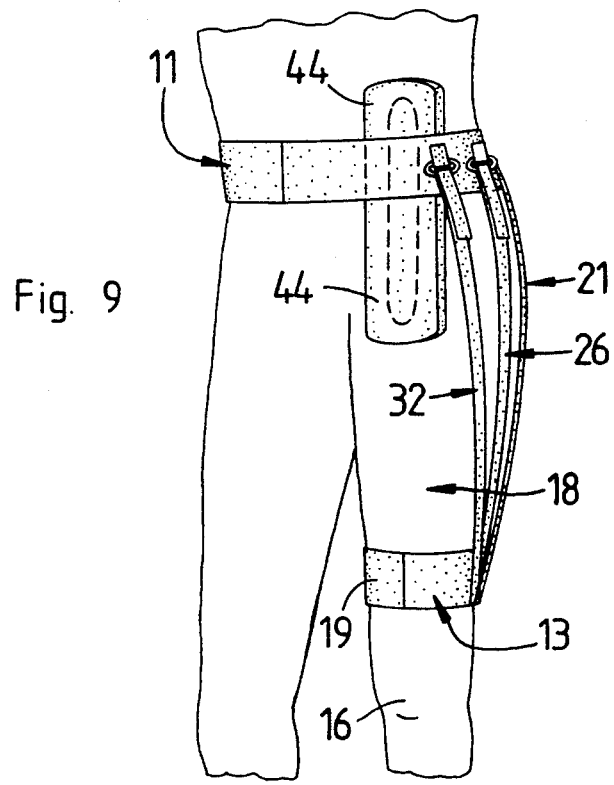
FIG. 9 is a perspective view of the lower abdomen and thigh regions of a human wearing a third embodiment of the present invention.

A third embodiment of the present invention is shown in FIG. 9 and contemplates the use of a padded, rigid member 44 placed intermediate the waist belt 11 and the patient's abdomen. The board 44 is placed forwardly of the ilium and extends downwardly across the front of the patient's thigh 18. The board severely restricts flexion of the thigh and is used in more severe cases when little or no movement of the thigh 18 is necessary. From the foregoing, it should be clear that the present apparatus represents a substantial improvement over the prior art.

While I have shown my invention in two forms, it will be obvious to those skilled in the art that it is not so limited but is susceptible of various changes and modifications without departing from the spirit thereof.

What we claim is:

1. Apparatus for limiting the movement of a patient's thigh to prevent inadvertent dislocation of the patient's femur from the patient's pelvic socket, said apparatus comprising:

(a) a flexible inelastic posterior strap fixably connected to a primary thigh belt wrapped around the patient's legs subjacent the muscle bulk of the patient's thigh and to a waist belt encircling the patient'waist such that said posterior strap will limit flexion of the patient's hip;

(b) a flexible inelastic medial strap fixably connected to said primary thigh belt adjacent said posterior strap and extending therefrom along the patient's tensor fascia latae and across the patient's greater trochanter, wherein said medial strap is connected to said waist belt laterally of said posterior strap to limit flexion of the patient's hip and adduction of the patient's thigh; and (c) a flexible inelastic anterior strap connected to said primary thigh belt adjacent said posterior strap and extending from said thigh strap along the anterior superior iliac spine, wherein said anterior strap is connected to said waist belt forwardly of said ilium to limit adduction of the patient's thigh.

2. Apparatus as defined in claim 1 further comprising a secondary thigh belt fixably connected to said flexible straps above said primary belt.

3. Apparatus as defined in claim 1 further comprising means for adjusting said flexible substantially inelastic straps to accommodate differences in the anatomical dimensions of various patient's.

4. Apparatus as defined in claim 1 wherein each said strap is connected to said primary thigh belt and extends therefrom upwardly and through one or more attachment members connected to said waist belt, wherein each said strap has securing means connected to a free end thereof for connecting said free end to said strap to secure said strap within said attachment member and to said waist belt.

5. Apparatus as described in claim 1 wherein said securing means comprises a hooked portion of hook and loop connector connected to said free end for securably engaging a looped portion of hook and loop connector connected to said strap.

6. Apparatus as defined in claim 1 further comprising a rigid member positioned intermediate said waist belt and the patient's abdomen and extending across the front of the patient's thigh to limit flexion of the patient's hip.

7. Apparatus for limiting the movement of a patient's leg to prevent inadvertent dislocation of the patient's femur from the patient's pelvic socket, said apparatus comprising:
   (a) a waist belt detachably secured about the patient's waist;
   (b) a primary thigh belt detachably secured about the patient's leg beneath the bulk of the thigh muscle;
   (c) a flexible substantially inelastic posterior strap connected to said primary thigh belt substantially rearwardly and laterally of the patient's thigh and extending from said thigh belt over the patient's gluteus maximus and through a posterior attachment member connected to said waist belt proximal to the patient's spinal column, such that said posterior strap may be adjusted to limit the forward flexion of the patient's hip;
   (d) a flexible substantially inelastic medial strap fixably connected to said primary thigh belt substantially rearwardly and laterally of the patient's thigh and extending from said primary thigh belt along the patient's tensor fascia latae, across the patient's greater trochanter and through a medial attachment member connected to said waist belt in laterally spaced relation to said posterior attachment member and superjacent the patient's ilium, such that said medial strap may be adjusted to limit flexion of the patient's hip and adduction of the patient's thigh; and
   (e) a flexible substantially inelastic anterior strap connected to said primary thigh belt substantially rearwardly and laterally of the patient's thigh and extending from said primary thigh belt along an anterior superior iliac spine of the patient's pelvis and through an anterior attachment member connected to said waist belt in laterally spaced relation to said medial attachment member and forwardly of the patient's ilium, such that said anterior strap may be adjusted to limit the adduction of the patient's thigh.

8. Apparatus as defined in claim 7 further comprising a secondary thigh belt fixably connected to said flexible substantially inelastic straps above said primary belt.

9. Apparatus as defined in claim 7 wherein each said flexible substantially inelastic strap extends upwardly from said primary thigh belt through one or more attachment members connected to said waist belt, and wherein each of said straps has securing means connected to a free end thereof for connecting said free end to said strap to secure said strap within said attachment member and to said waist belt.

10. Apparatus as defined in claim 9 wherein said securing means comprises a hooked portion of hook and loop connector connected to said free end for securably engaging a looped portion of hook and loop connector connected to said strap.

* * * * *